(12) United States Patent
Aksimentiev

(10) Patent No.: US 9,404,909 B2
(45) Date of Patent: Aug. 2, 2016

(54) METHOD AND APPARATUS FOR CONTROLLING MATERIALS THROUGH A THROUGH-HOLE

(71) Applicant: THE BOARD OF TRUSTEES OF THE UNIVERSITY OF ILLINOIS, Urbana, IL (US)

(72) Inventor: Aleksei Aksimentiev, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 560 days.

(21) Appl. No.: 13/911,333

(22) Filed: Jun. 6, 2013

(65) Prior Publication Data
US 2014/0360876 A1   Dec. 11, 2014

(51) Int. Cl.
G01N 27/447   (2006.01)
G01N 33/487   (2006.01)
C12Q 1/68     (2006.01)

(52) U.S. Cl.
CPC ........ *G01N 33/48721* (2013.01); *C12Q 1/6869* (2013.01)

(58) Field of Classification Search
CPC ..... G01N 27/3275–27/3278; G01N 33/48721; C01B 31/04; C01B 31/0438; C01B 2204/00–2204/32
See application file for complete search history.

(56) References Cited

U.S. PATENT DOCUMENTS

2011/0226623 A1* 9/2011 Timp ............... G01N 33/48721
                                                       204/543
2012/0234679 A1* 9/2012 Garaj .................... B82Y 30/00
                                                       204/520

OTHER PUBLICATIONS

Wells, David B. et al., "Assessing Graphene Nanopores for Sequencing DNA", Nano Letters, vol. 12, pp. 4117-4123, 2012.
Branton, Daniel et al., "The potential and challenges of nanopore sequencing", Nature Biotechnology, 26(10), pp. 1146-1153, Oct. 2008.
Cherf, Gerald M. et al., "Automated forward and reverse ratcheting of DNA in a nanopore at 5-A precision", Nature Biotechnology, 30(4), pp. 344-348, Apr. 2012.
Manrao, Elizabeth A. et al., "Reading DNA at single-nucleotide resolution with a mutant MspA nanopore and phi29 DNA polymerase", Nature Biotechnology, Advance Online Publication, pp. 1-6, http://www.nature.com/naturebiotechnology/, Mar. 25, 2012.

* cited by examiner

*Primary Examiner* — J. Christopher Ball
(74) *Attorney, Agent, or Firm* — Guntin & Gust, PLC; Ed Guntin

(57) ABSTRACT

A system that incorporates the subject disclosure may include, for example, a method for selectively applying an electrical potential to a top surface of a membrane having a nanopore to repel or attract a molecular strand from the top surface of the membrane, applying a second electrical potential to a bottom surface of the membrane to repel or attract the molecular strand from the bottom surface of the membrane, applying a third electrical potential to an electrolyte solution to apply a transport force on the molecular strand to displace a section of the molecular strand into the nanopore, arresting the section of the molecular strand in the nanopore by adjusting of the first electrical potential, the second electrical potential, the third electrical potential, or combinations thereof, and measuring a signal at the nanopore to identify the section of the molecular strand. Other embodiments are disclosed.

20 Claims, 11 Drawing Sheets

US 9,404,909 B2

METHOD AND APPARATUS FOR CONTROLLING MATERIALS THROUGH A THROUGH-HOLE

STATEMENT AS TO FEDERALLY SPONSORED RESEARCH

This invention was made with government support under contract number R01HG05115 awarded by the National Institutes of Health and contract number DMR0955959 awarded by the National Science Foundation. The Government has certain rights in the invention.

FIELD OF THE DISCLOSURE

The subject disclosure relates to a method and apparatus for controlling materials through a through-hole.

BACKGROUND

It has been suggested that nanopores in thin membranes can be used to detect and characterize nucleic acids polymers DNA and RNA, including their nucleotide sequence [1]. In the very basic setup, a lipid bilayer membrane containing a single nanopore in it is submerged in electrolyte solution containing dissolved analyte molecules. External electric field forces charged analytes to transit the nanopore from one side of the membrane to the other, modulating the current of ions flowing through the nanopore. It has been shown that biological nanopores MspA [2] and alpha-hemolysin [3] can be used to read out the sequence of single DNA strands as modulations of the ionic current if the transport of DNA through the nanopores is controlled by auxiliary protein motors such as a DNA polymeraze.

Nanopores in solid-state membranes are thought to have even greater potential for biosensing applications, as they exhibit superior mechanical properties and can be straightforwardly integrated with conventional electronics for large array multiplex detection. However, the common problem with using solid-state nanopores for DNA sequencing and other biosensing applications is the lack of control over the transport of DNA through the nanopores. Typically, the DNA transits a solid-state nanopore too fast for its sequence to be detected by a physical measurement.

BRIEF DESCRIPTION OF THE DRAWINGS

Reference will now be made to the accompanying drawings, which are not necessarily drawn to scale, and wherein.

DETAILED DESCRIPTION

The subject disclosure describes, among other things, illustrative embodiments for controlling materials through a through-hole device. Other embodiments are included in the subject disclosure.

The subject disclosure describes among other embodiments methods for controlling the transport of DNA through single layer and multi-layer graphene nanopores, positioning of the DNA nucleotides to enable their identification via a physical measurement and increasing the throughput of the nanopore sensing. A discovery relevant to the subject disclosure is hydrophobic sticking of DNA bases to the surface of graphene that was found to control the rate of DNA transport through nanopores. Examination of molecular dynamics simulations of graphene nanopore systems suggest that the strength of DNA adhesion to graphene can be modulated by changing the electrostatic potential of the graphene membrane. Electrostatic control over DNA adhesion can be used to control the transport of DNA through the nanopore.

The subject disclosure describes embodiments for transporting DNA in single nucleotide steps of prescribed durations. The time interval between the steps can be used to detect the sequence of nucleotides using various methods, for example, by measuring the ionic current through the nanopore, the transverse tunneling current or transverse nanoribbon conductance or yet another means, such as Raman and other spectroscopy methods.

Embodiments of the subject disclosure can have practical applications in the area of nanopore sequencing of DNA. The principle described in the subject disclosure is neither limited to graphene nanopores nor to nucleic acid analytes and can be applied to other materials and target systems, for example, protein detecting and sequencing, genotyping and in other biosensing applications.

Embodiments of the subject disclosure include among other things: (a) methods to control transport of single-stranded DNA through a nanopore in a free-standing graphene membrane; and (b) methods to control transport of single-stranded DNA through a nanopore in a stacked graphene-insulator membrane.

In one embodiment, these methods can be combined to form a system for DNA sequencing. In one embodiment, the subject disclosure describes graphene as a material used to control DNA motion. The methods described can be also applied to other atomically smooth conducting materials. Similarly, characterization of other biomacromolecules such as RNA and unfolded proteins can be the target applications of the subject disclosure.

Methods to control transport of single-stranded DNA through a nanopore in a free-standing graphene membrane are further described below.

Figure 1:
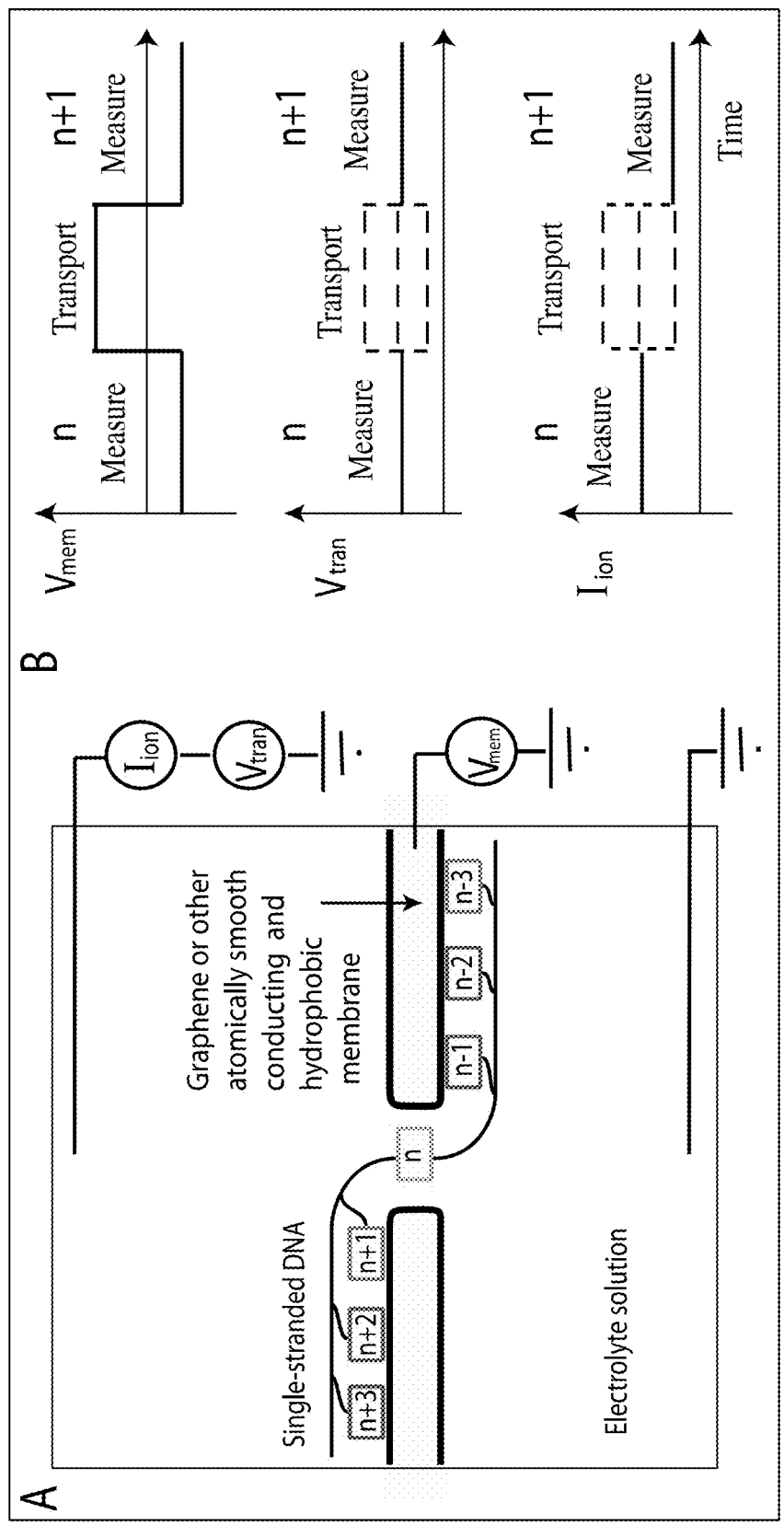
FIG. 1 depicts an illustrative embodiment of a system for controlled motion of single-stranded DNA (ssDNA) through a free-standing graphene membrane.

First, we consider the case of a freestanding single-layer graphene membrane as shown in FIG. 1. FIG. 1 depicts an illustrative embodiment of a system for controlled motion of single-stranded DNA (ssDNA) through a free-standing graphene membrane. Section (A) of FIG. 1 illustrates schematics showing a nanopore in a graphene membrane and a single DNA strand threaded through the nanopore. In the state shown in the figure, the membrane is neutral, which facilitates hydrophobic adhesion of DNA bases to its surface.

Individual nucleotides of the DNA strand are shown as squares and numbered ascending from one end of the strand to the other. The membrane is submerged in electrolyte solution and is connected to electro-motive voltage source. Another voltage source is connected, through the current meter, to an electrode submerged in an electrolyte solution on one side of the membrane; the solution on the other size of the membrane is electrically grounded. Section (B) of FIG. 1 illustrates schematics showing measured (Iion) and control (V_tran and V_mem) variables during a typical operation cycle of the device.

The gray background highlights one operation cycle. The measurement (Iion) is taken when the DNA strand's motions through the nanopore (driven by V_tran) is arrested by the hydrophobic adhesion to the membrane strengthened by its negative charge. To transport the DNA strand through the pore in controlled steps, electric potentials V_mem are changed, lowering the adhesion of the DNA strand to the membrane. Changes in the transmembrane bias V_tran may occur simultaneously with the changes in the membrane potential Vmem to achieve the desired transport of the DNA strand.

After a desirable number of DNA nucleotides transported through the nanopore, the membrane potential V_mem return to its "trapping" value and the measurements of Iion are performed. The profiles of the transmembrane potential and the ionic currents are shown for illustration purpose only and may appear different in the actual device. Ionic current measurement may be augmented by a different DNA sequence detection modality, for example, transverse tunneling current or measurements of the graphene conductance.

Panel A of FIG. 1 schematically shows a system for sequencing DNA that contains a free-standing graphene membrane with a single DNA strand threaded through a nanopore in the membrane. The voltage difference across the membrane V_tran drives ions dissolved in the electrolyte solution through the nanopore; the resulting ionic current I_ion is recorded via a measuring apparatus, for example, ampere-meter. The transmembrane potential V_tran also applies an electrophoretic force to a DNA strand, which, at certain conditions, can transport the DNA strand through the nanopore. The electrostatic potential of the membrane is controlled by the voltage source V_mem. Changing the electrostatic potential of the membrane alters affinity to the DNA strand to the graphene membrane, allowing its transport to be precisely controlled. To measure the nucleotide sequence of a DNA strand, the latter is transported through the nanopore in discrete steps while its sequence is determined by measuring the nanopore ionic current (I_ion).

Figure 2:
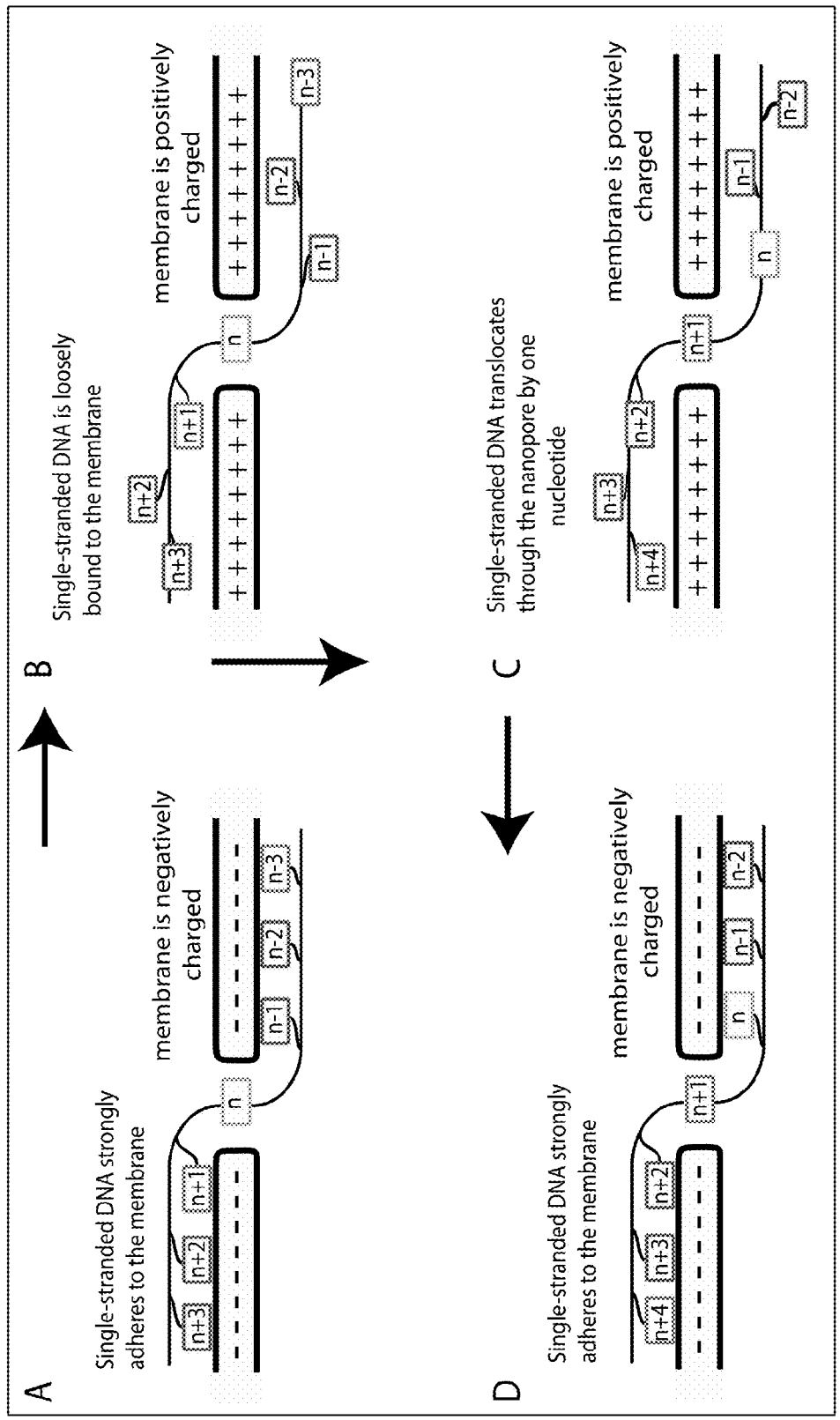
FIG. 2 depicts an illustrative embodiment of a schematic illustration of one operation cycle of the free-standing graphene nanopore sensor.

FIG. 2 depicts an illustrative embodiment of a schematic illustration of one operation cycle of the free-standing graphene nanopore sensor. Section (A) of FIG. 1 illustrates a DNA strand is hold in place by strong hydrophobic adhesion to the membrane strengthened by its negative charge while the nanopore ionic current reports on the type of DNA nucleotide n. Section (B) of FIG. 2 illustrates the DNA strand's adhesion to the membrane is decreased by assigning a positive charge to the membrane The membrane's charge is regulated by the membrane potential V_mem. Section (C) of FIG. 2 illustrates the DNA strand being displaced through the nanopore driven by the transmembrane bias V_tran. Section (D) of FIG. 2 illustrates that after the DNA strand has been displaced by one nucleotide, the membrane bias V_mem is switched back to a negative value, which enhances adhesion of ssDNA to the membrane and arrests the translocation. The ionic current reports on the type of DNA nucleotide n+1.

FIG. 2 schematically illustrates one operation cycle of the nanopore system. Panels A and D of FIG. 2 illustrate the biosensing part of the cycle, where the type of nucleotide n (panel A) and n+1 (panel D) is determined by measuring the nanopore ionic current. Between these two states, the DNA strand is displaced by one nucleotide by changing the electric potential of the graphene membrane (V_mem). To initiate the displacement, the membrane is first positively charged to loosen hydrophobic adhesion of DNA nucleotides (panel B). Following that, the DNA strand is displaced through the nanopore driven by the transmembrane bias V_tran (panel C).

The sign and value of V_tran can to be adjusted from its "measurement" value for exercise control over the direction and the number of DNA nucleotides transported within one cycle, respectively. Following that, the membrane potential V_mem is changed to negatively charge the membrane; the value of the transmembrane bias V_tran might have to be adjusted as well. Charging negatively the membrane strengthens adhesion of the DNA strand to the surface of the membrane and arrests its transport through the nanopore (panel D). States shown in panels A and D of FIG. 2 are equivalent and differ only by the displaced nucleotides.

A physical effect underlying the subject disclosure is the control over adhesion of DNA to the surface of a graphene membrane by changing the electrostatic potential of the membrane with respect to the solution. Charging of the membrane produced by the change of the electrostatic potential dramatically affects the conformation of the biopolymer.

Figure 3:
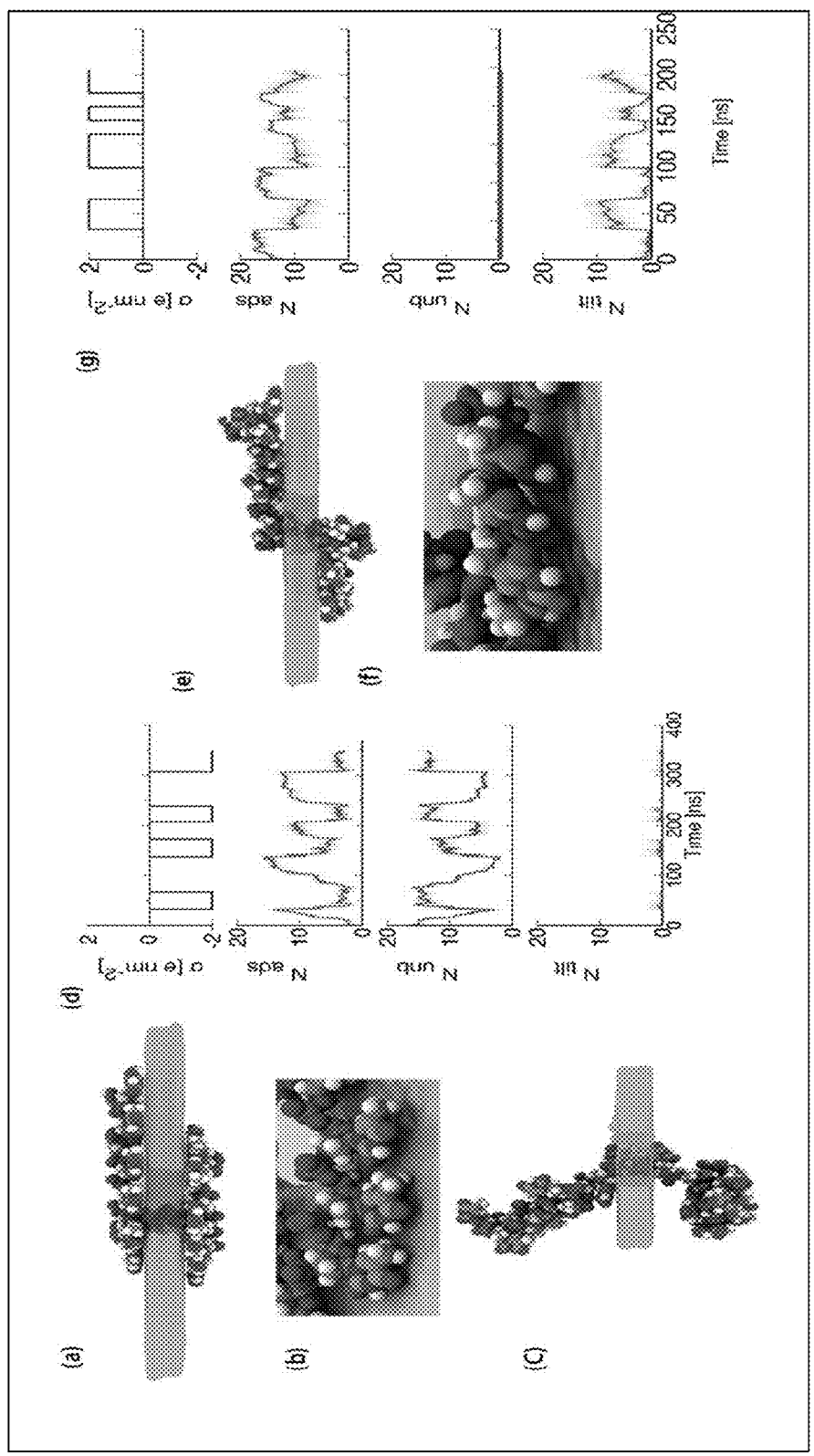
FIG. 3 depicts an illustrative embodiment of the charge of a graphene membrane controls the conformation of ssDNA.

FIG. 3 depicts an illustrative embodiment of the charge of a graphene membrane controls the conformation of ssDNA. Section (a) of FIG. 3 illustrates a conformation of ssDNA threaded through a nanopore in a neutral graphene membrane. Section (b) of FIG. 3 illustrates an enlarged view of ssDNA shown bound to a neutral graphene membrane. The bases of ssDNA adhere to graphene. Section (c) of FIG. 3 illustrates a conformation of ssDNA threaded through a negatively charged graphene membrane; the graphene surface charge density is $-2$ $e/nm^2$, where e is the charge of a proton. Section (d) of FIG. 3 illustrates a variation of the membrane charge a produces reversible changes in the conformation of ssDNA. The graphs show the variation of the number of adsorbed (N_ads), unbound (N_unb) and tilted (N_tilt) nucleotides of the 20-nucleotide DNA strand. Section (e) of FIG. 3 illustrates a conformation of ssDNA threaded through a nanopore a positively charged graphene membrane ($\rho=2$ $e/nm^2$). Section (f) of FIG. 3 illustrates an enlarged view of ssDNA at the surface of a positively charged graphene membrane. The bases remain attached to graphene but tilt with respect to the graphene surface. Section (g) of FIG. 3 illustrates a variation of the membrane charge a produces reversible changes in the conformation of ssDNA. The graphs show the variation of the number of adsorbed (N_ads), unbound (N_unb) and tilted (N_tilt) nucleotides of the 20-nucleotide DNA strand.

FIG. 3 illustrates the effect by showing the typical conformations of single stranded DNA (ssDNA) threaded through a graphene nanopore when the membrane is neutral FIG. 3a,b), negatively charged (FIG. 3c), and positively charged (FIG. 3e,f). When the graphene membrane is neutral (its electrostatic potential is zero), the DNA adheres to its surface due to hydrophobic interactions between the DNA bases and the graphene. Giving the membrane a negative charge (by mean of applying an electrostatic potential that is negative with respect to the solution) repels negatively charged DNA, resulting in the dramatic change of the DNA's conformation. The change of the conformation is reversible, so that when the membrane becomes neural again, ssDNA adheres it (FIG. 3d).

Applying a positive bias alters the DNA conformation as well: the bases tilt with respect to the plane of the graphene membrane. The changes are reversible so that the conformation of the DNA can be controlled by changing the potential of the membrane (FIG. 3g). Although we use here a specific example of ssDNA adhesion to graphene, the physical principle is not limited to these two materials. The principle is applicable to any polymer and membrane as long as the polymer carries electric charge and contains hydrophobic groups that can adhere to the surface of a hydrophobic and conducting membrane.

Figure 4:
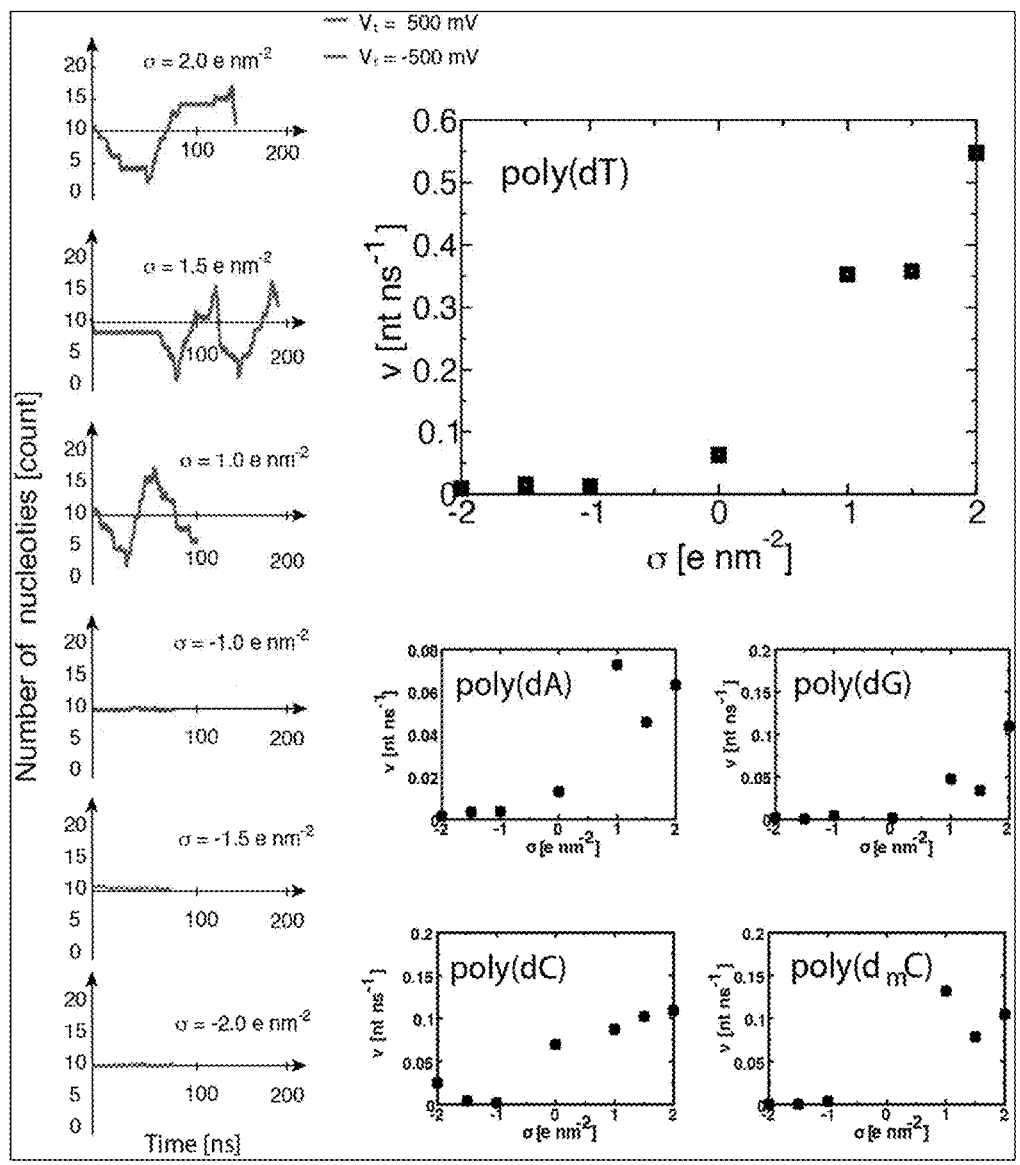
FIG. 4 depicts an illustrative embodiment of a molecular dynamics simulations of ssDNA translocation through a nanopore in charged graphene membranes.

FIG. 4 depicts an illustrative embodiment of a molecular dynamics simulations of ssDNA translocation through a nanopore in charged graphene membranes. A right side of FIG. 4 illustrates the number of DNA nucleotides in one of the compartments versus time in the simulations of poly(dT)$_{20}$ translocation through nanopores in graphene membranes of surface charge density $\sigma$. Some of the systems were simulated at both positive and negative signs of the transmembrane bias $V_t$. A left side of FIG. 4 illustrates the average translocation velocity of poly(dT)$_{20}$, poly(dA)$_{20}$, poly(dG)$_{20}$, poly(dC)$_{20}$, poly(dmC)$_{20}$ versus the surface charge density under a 500 mV transmembrane bias. The translocation velocity is close to zero for negatively-charged membranes and increases with the charge density regardless of the sequence of the DNA strand.

FIG. 4 demonstrates the effect of the graphene charge on the velocity of ssDNA translocation through a graphene nanopore. In this set of simulations, a constant transmembrane bias V_tran was applied to several graphene systems having different surface charge density $\sigma$. For the two-layer graphene membrane featured in the figure, the nanopore transport of ssDNA is arrested when the graphene membrane is negatively charged. The translocation is accelerated when graphene is positively charged. Similar effect is seen for all DNA homopolymers. Thus, the velocity of electrophoretic transport of ssDNA through a nanopore in graphene can be regulated by changing the charge of the graphene membrane. The latter can be done, for example, by changing the electrical potential of the membrane. The actual response of ssDNA velocity to the charge of the graphene membrane depends on the number of graphene layers in the membrane and the charge of the atoms immediately surrounding the nanopore.

Figure 5:
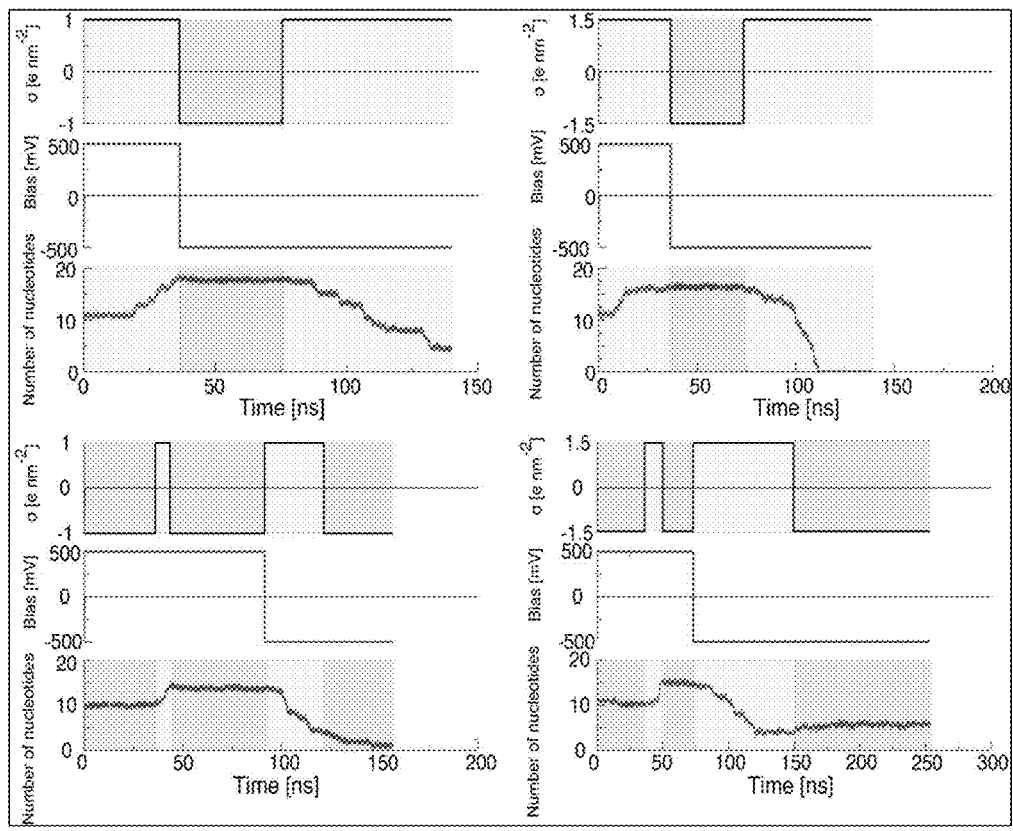
FIG. 5 depicts an illustrative embodiment of a velocity of DNA translocation can be regulated by the charge state of the graphene membrane.

FIG. 5 depicts an illustrative embodiment of a velocity of DNA translocation can be regulated by the charge state of the graphene membrane. Each of the four panels shows three sets of graphs that indicate the surface charge density of the graphene membrane $\sigma$, the transmembrane bias and the number of DNA nucleotides in one of the compartments versus the simulation time. Changing the charge density from a positive to negative value arrests translocation of ssDNA through a nanopore. Changing the charge density from a negative to positive values resumes ssDNA translocation through a nanopore. Thus, DNA transport velocity can be regulated by the charge state of the graphene membrane.

FIG. 5 illustrates the use of the graphene membrane charge state to alter the velocity of ssDNA translocation through a nanopore. In these simulations, the speed of the electrophoretic transport of DNA through a nanopore is reduced by negatively charging the graphene membrane and increased by positively charging the graphene membrane. Both FIGS. 4 and 5 demonstrate the feasibility of the proposed method for controlling the velocity of ssDNA transport through graphene membrane.

Methods to control transport of single-stranded DNA through a nanopore in a stacked graphene-insulator membrane are further described below.

FIG. 5 shows a multi-layer nanopore system that offers precise control over the stepwise motion of DNA. The simplest device of that kind contains two graphene membranes separated by a layer of dielectric. The electrostatic potentials of the top and bottom membranes, V_top and V_bot, are independently regulated, which allows for independent control of the conformations of the DNA strand at different sides of the nanopore. Another pair of electrodes imposes a bias of electrostatic potential across the membrane, V_tran, which produces transport of charged solutes (e.g., DNA, proteins, ions) through the nanopore. Driven by the transmembrane bias, ionic current is measured by a current meter. The multi-layer setup enables additional biosensing functionality such as transverse tunneling current or nanoribbon conductance measurement or emission excitation readouts.

FIG. 5 schematically illustrates one operation cycle of such a control system. The top and bottom images illustrate the biosensing states of the cycle, where the types of nucleotides n (top) and n+1 (bottom) are characterized through ionic current, transverse tunneling or other measurement. The diagram on the left illustrates the sequence of events that result in displacement of the DNA strand by one nucleotide forward. The diagram on the right illustrates the sequence of events that step the DNA backwards by one nucleotide.

In the "biosensing" state, both parts of the strand are kept at the surface of the membrane due to hydrophobic and electrostatic interactions between the strand and the graphene membranes. By changing the charge of the top (or bottom) membrane, the affinity of the top (or bottom) part of the strand can be reversibly modulated. At the same time, the strand can be transport through the nanopore by the electric field that originates from the charge difference between the top and bottom graphene layers. Thus, the value of the graphene's electrical potentials with respect to the ground $V_{top}$ and $V_{bottom}$ control the strength of ssDNA adhesion to graphene whereas the difference in the potentials ($V_{top}-V_{bottom}$) controls the direction of ssDNA motion through the nanopore.

The velocity of the translocation depends on both the actual values of the top and bottom electrodes and their difference. The transmembrane bias $V_{tran}$ is used to initially capture and drive the DNA strand into the nanopore. Optionally, $V_{tran}$ can be used to fine-tune the distribution of the electric field inside the nanopore. Stretching the DNA strand in the nanopore under the influence of the electric field enable precise control over the stepping mechanism. That is, when a stretched DNA strand is released (by changing the charge of the membrane), it will contract in a highly reproducible manner, which enables single nucleotide stepping by rapidly switching the potential back to the "trapping" value shortly after releasing the strand.

The major advantage of this invention is rapid (<1 ns) control over ssDNA desorption from the membrane, which is made possible by local switching of the electrostatic potential. The rapid switching of the potential is essential to exercise precise control over transport of biomolecules. The same principle can be applied to transport of proteins that contain both charged and hydrophobic groups and could be one of the key enabling technology for nanopore sequencing of proteins.

Figure 6:
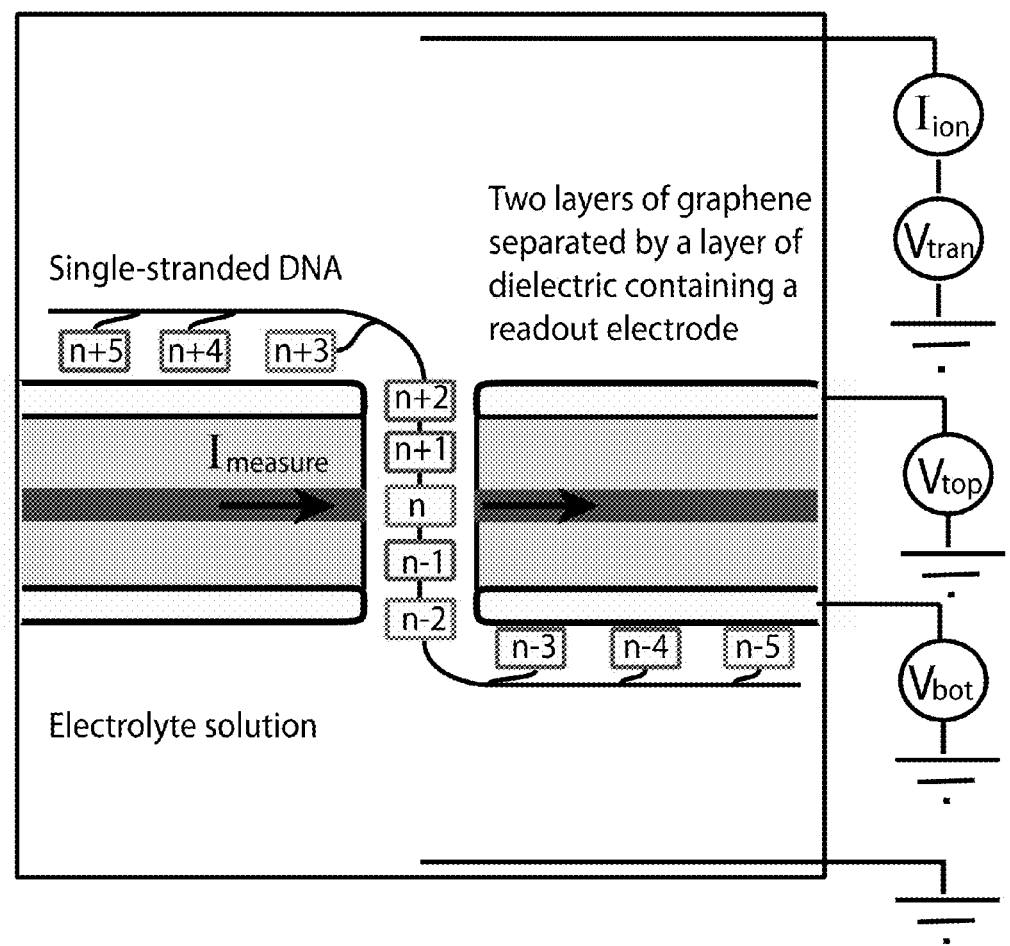
FIG. 6 depicts an illustrative embodiment of schematics of a multi-layer nanopore system for controlled transport and characterization of biomacromolecules.

FIG. 6 depicts an illustrative embodiment of schematics of a multi-layer nanopore system for controlled transport and characterization of biomacromolecules. Two graphene membranes are separated by a layer of dielectric that may contain biosensing probes. A transverse conductance probe is shown as an example. A strand of DNA is threaded through the nanopore. The nucleotides of the strand are schematically shown as rectangles numbered according to the order of nucleotides in the strand. The nucleotides of the DNA strand away from the nanopore adhere so the graphene membranes. The potential of each graphene membrane can be independently controlled to regulate the adsorption strength of DNA to the membrane and transport the DNA through the nanopore. In addition to the two membrane potentials V_top and V_bot, a transmsmbrane bias V_tran can electrophoretically transport DNA through the nanopore and generate ionic current I_ion.

Figure 7:
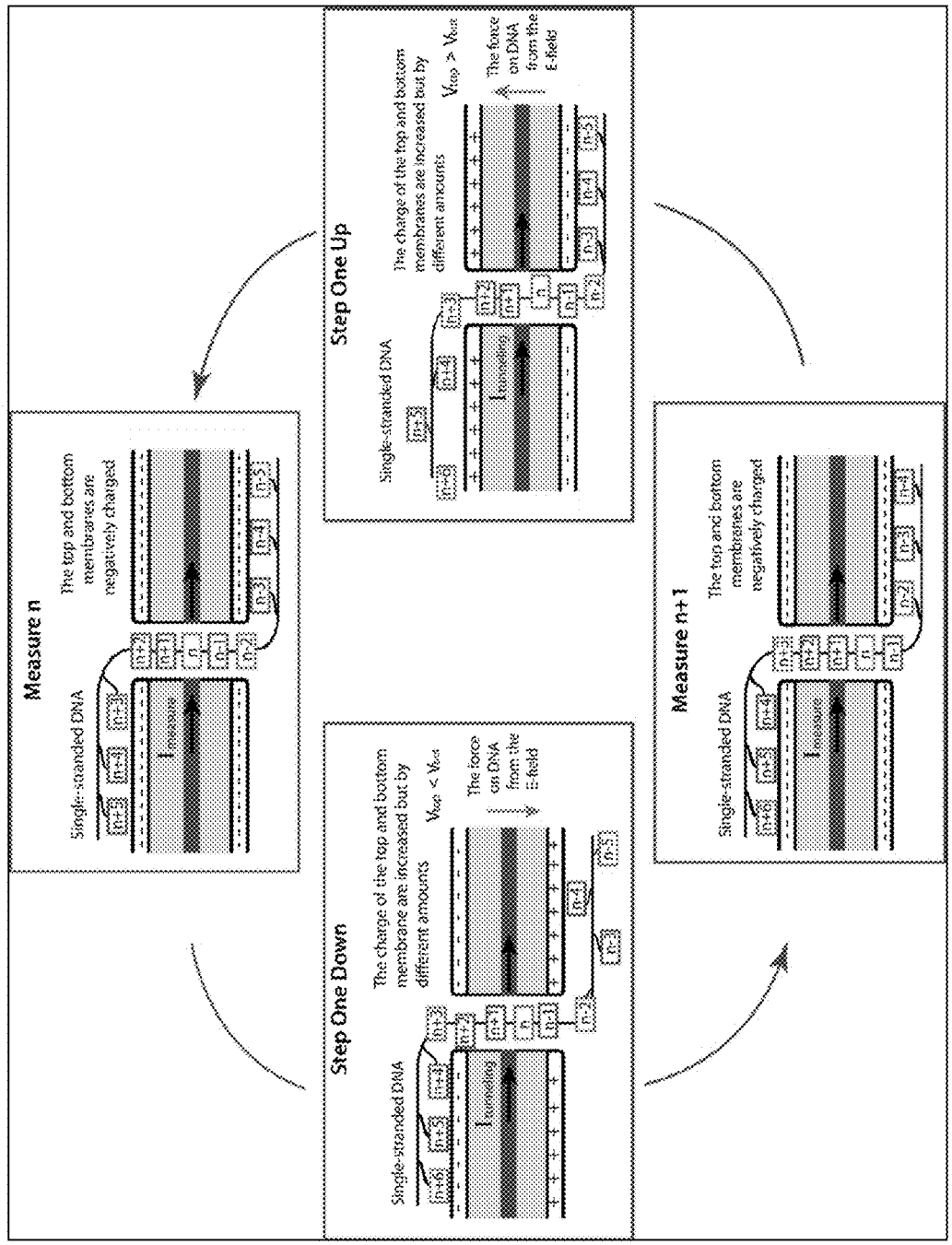
FIG. 7 depicts an illustrative embodiment of reversible stepping of ssDNA through a stacked-graphene membrane system.

FIG. 7 depicts an illustrative embodiment of reversible stepping of ssDNA through a stacked-graphene membrane system. A panel depicted as (Measure n) of FIG. 7 illustrates that the DNA strand is held in place by hydrophobic adhesion and electrostatic interactions with the top and bottom graphene layers. The DNA sequence measurement is performed by either recording the nanopore ionic current and/or the current through the third electrode embedded in the middle of the membrane. A panel depicted as (Step One Down) of FIG. 7 illustrates that to produce a one-nucleotide (or larger) displacement of the DNA strand through the nanopore, the potential $V_{top}$ and $V_{bottom}$ are changed to alter the charge states of the top and bottom graphene layers. To move the DNA by one nucleotide down, the potential of the bottom membrane must be larger than the potential of the top membrane.

The actual velocity of the DNA is controlled by both the potential difference between the top and bottom electrodes and their absolute values. For the two carbon layer graphene sheets, positively biasing the membrane reduces adhesion of ssDNA and thus moving DNA down by one nucleotide would require loosening of the DNA adhesion by increasing the charge of both top and bottom membranes and making the bottom membrane having a higher potential then the top membrane. A panel depicted as (Measure n+1) of FIG. 7 illustrates that the DNA strand is held in place by hydrophobic adhesion and electrostatic interactions with the top and bottom graphene layers. The DNA sequence measurement is performed by either recording the nanopore ionic current and/or the current through the third electrode in the middle of the membrane. A panel depicted as (Step One Up) of FIG. 7 illustrates that to move the DNA up by one nucleotide, the strength of DNA adhesion to the membrane can be lessened by rising the potential of both top and bottom layers while assigning the top layer a higher potential then of the bottom layer.

Figure 8:
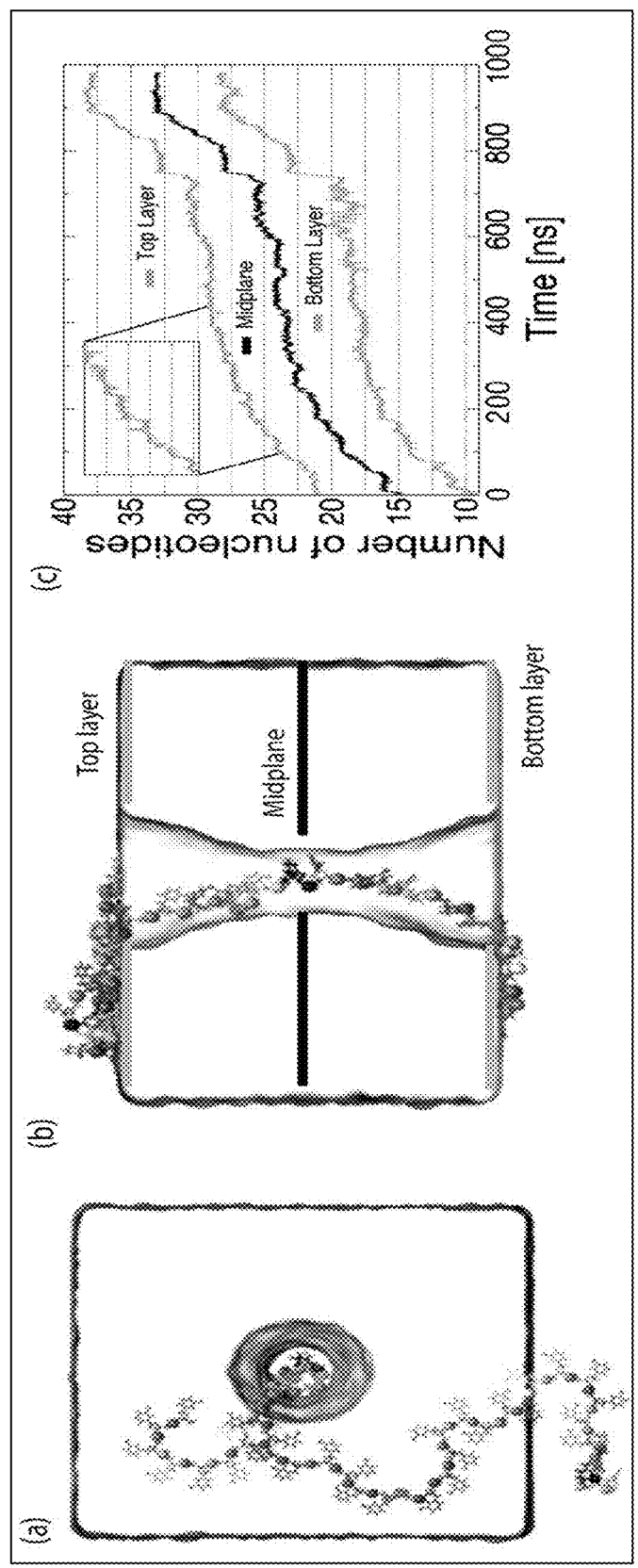
FIG. 8 depicts an illustrative embodiment of molecular dynamics simulations of ssDNA translocation through a stacked graphene nanopore system.

FIG. 8 depicts an illustrative embodiment of molecular dynamics simulations of ssDNA translocation through a stacked graphene nanopore system. (a, b) Top and side views of the simulation system. A 5-nm insulator membrane (SiO2) is sandwiched between two layers of graphene (not shown in panel a). A 56-nucleotide strand of ssDNA is threaded through a nanopore. The system contains 1 M aqueous solution of KCl (not shown) (c) Molecular dynamics simulation of ssDNA translocation through a stacked graphene nanopore system. The translocation is driven by a transmembrane potential Vtran=500 mV. The top and bottom graphene sheets are electrically neutral. The plot shows the number of DNA nucleotides below the top, middle and bottom planes of the membrane versus simulation time. The planes are schematically shown in panel b. The DNA is observed to move through the nanopore in discrete steps. During the simulation, the DNA remained a stretched conformation, so that the number of nucleotides that adhered to the bottom graphene surfaces was equal to the number of nucleotides desorbed from the top surface.

Figure 9:
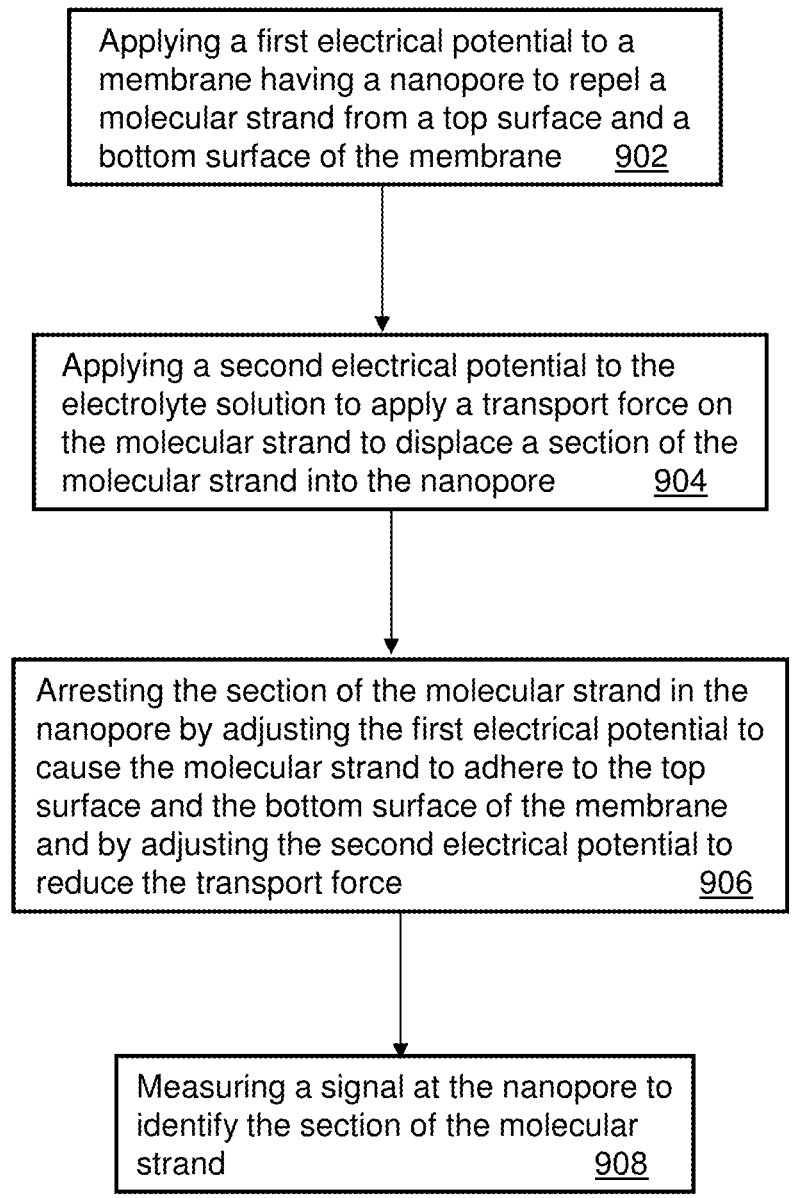
FIGS. 9-10 depicts an illustrative embodiment of methods applicable to the subject disclosure.

FIG. 9 depicts a method of the subject disclosure. The method can begin with step 902 where a first electrical potential is applied to a membrane having a nanopore to repel a molecular strand from a top surface and a bottom surface of the membrane, where the membrane and the molecular strand are placed in an electrolyte solution. At step 904, a second electrical potential can be applied to the electrolyte solution to apply a transport force on the molecular strand to displace a section of the molecular strand into the nanopore. At step 906 the section of the molecular strand in the nanopore can be arrested by adjusting the first electrical potential to cause the molecular strand to adhere to the top surface and the bottom surface of the membrane and by adjusting the second electrical potential to reduce the transport force. At step 908 a signal at the nanopore can be measured to identify the section of the molecular strand.

Figure 10:
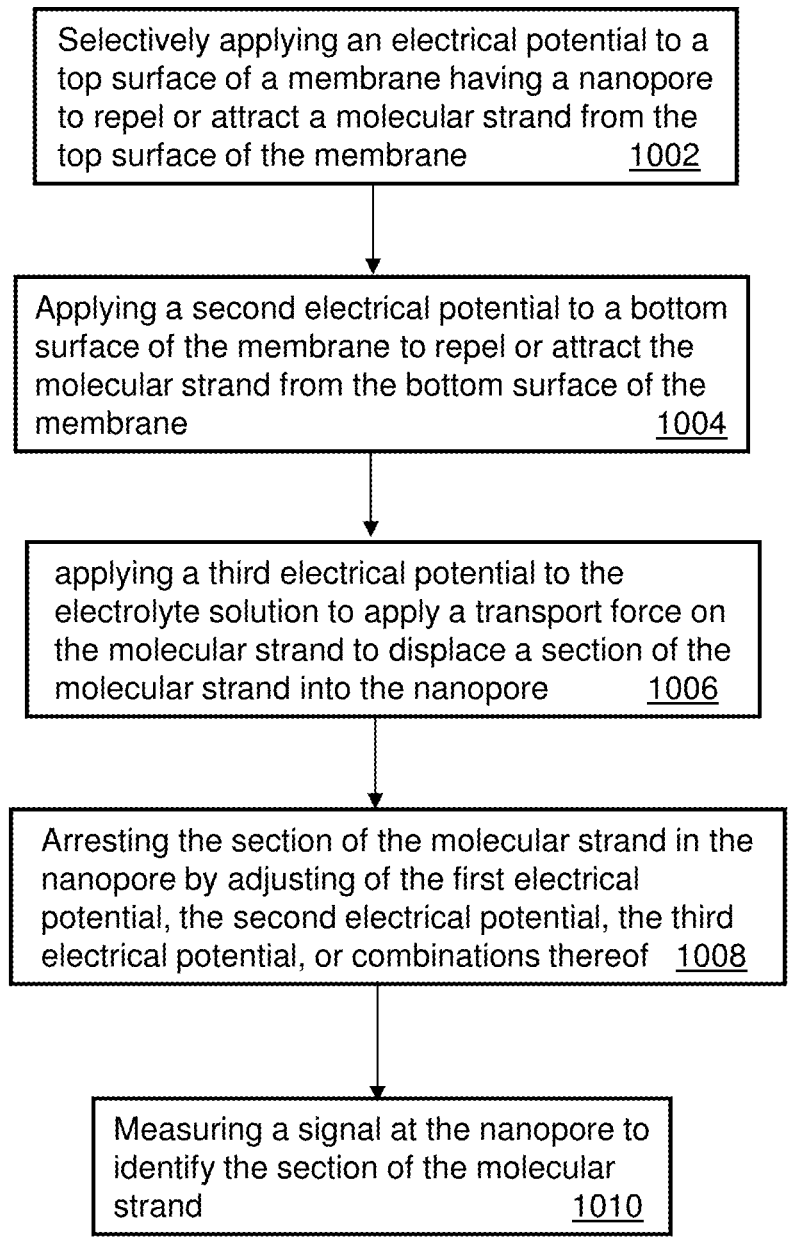

FIG. 10 depicts a method of the subject disclosure. The method can begin with step 1002 where a first electrical potential is applied to a top surface of a membrane having a nanopore to repel or attract a molecular strand from the top surface of the membrane, where the membrane and the molecular strand are placed in an electrolyte solution. At step 1004, a second electrical potential can be applied to a bottom surface of the membrane to repel or attract the molecular strand from the bottom surface of the membrane. At step 1006, a third electrical potential can be applied to the electrolyte solution to apply a transport force on the molecular strand to displace a section of the molecular strand into the nanopore. At step 1008, the section of the molecular strand in the nanopore can be arrested by adjusting of the first electrical potential, the second electrical potential, the third electrical potential, or combinations thereof. At step 1010, a signal at the nanopore can be measured to identify the section of the molecular strand.

Figure 11:
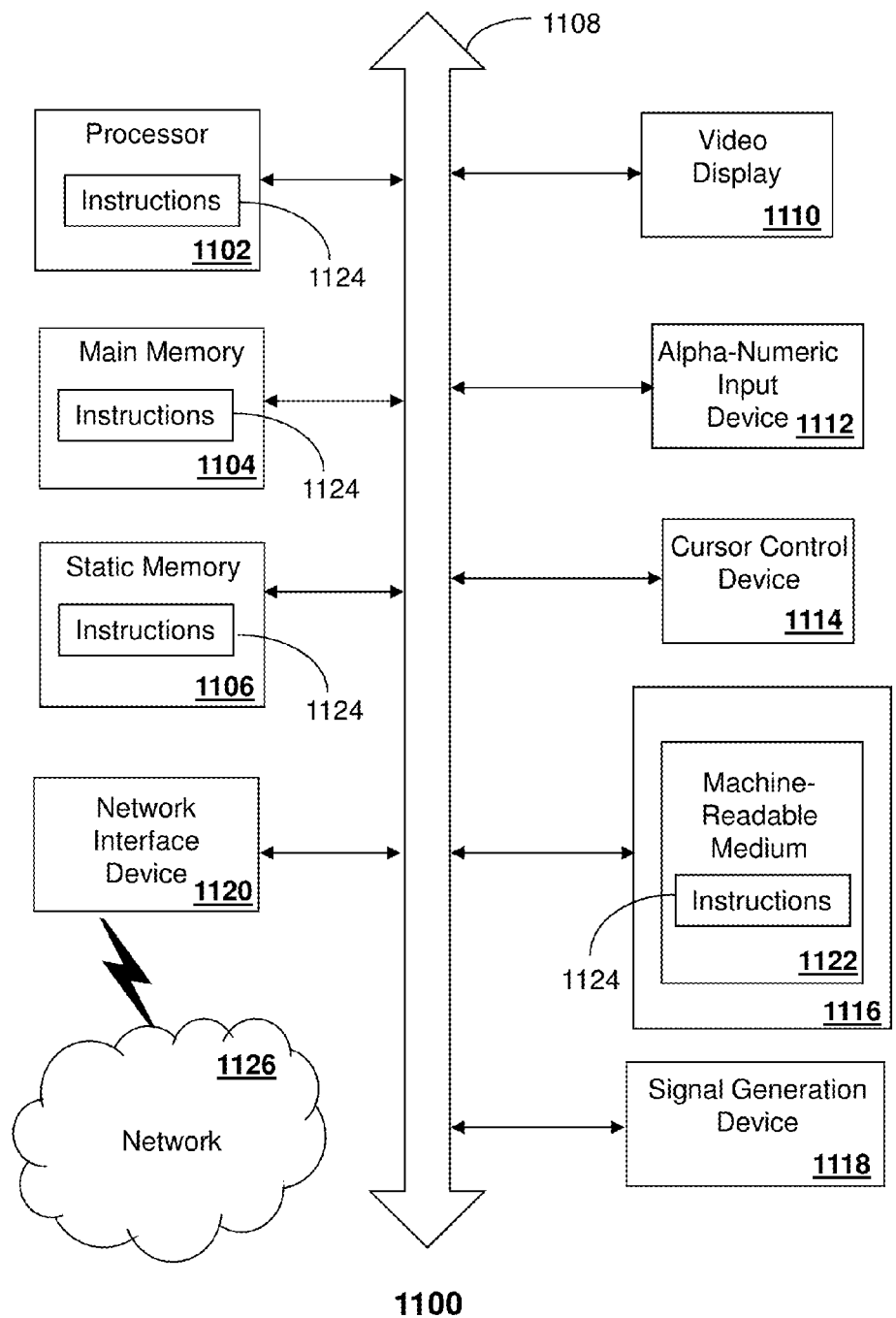
FIG. 11 is a diagrammatic representation of a machine in the form of a computer system within which a set of instructions, when executed, may cause the machine to perform any one or more of the methods described herein.

FIG. 11 depicts an exemplary diagrammatic representation of a machine in the form of a computer system 1100 within which a set of instructions, when executed, may cause the machine to perform any one or more of the methods described above. The machine in whole or in part can be combined with other apparatuses such as those illustrated in FIG. 1(A) or 6. For example, the machine can be combined with an apparatus including a membrane comprising a through-hole, a first voltage source to apply a first potential to a surface of the membrane, a second voltage source to apply a second potential to a solution having conductive properties, a sensor to measure a signal at the through-hole, a memory to store instructions, and a controller coupled to the memory, the first voltage source, the second voltage source, and the sensor.

Responsive to executing the instructions, the controller can perform operations including applying the first potential to the membrane to repel a molecular strand from one of a top surface of the membrane, a bottom surface of the membrane or both, wherein the membrane and the molecular strand are disposed in the solution, applying the second potential to the solution to apply a transport force on the molecular strand to displace a section of the molecular strand into the through-hole, arresting the section of the molecular strand in the through-hole by adjusting the first potential, the second potential, or both, and measuring the signal at the through-hole to identify the section of the molecular strand.

In some embodiments, the machine may be connected (e.g., using a network 1126) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 1100 may include a processor (or controller) 1102 (e.g., a central processing unit (CPU), a graphics processing unit (GPU, or both), a main memory 1104 and a static memory 1106, which communicate with each other via a bus 1108. The computer system 1100 may further include a display unit 1110 (e.g., a liquid crystal display (LCD), a flat panel, or a solid state display. The computer system 1100 may include an input device 1112 (e.g., a keyboard), a cursor control device 1114 (e.g., a mouse), a disk drive unit 1116, a signal generation device 1118 (e.g., a speaker or remote control) and a network interface device 1120. In distributed environments, the embodiments described in the subject disclosure can be adapted to utilize multiple display units 1110 controlled by two or more computer systems 1100. In this configuration, presentations described by the subject disclosure may in part be shown in a first of the display units 1110, while the remaining portion is presented in a second of the display units 1110.

The disk drive unit 1116 may include a tangible computer-readable storage medium 1122 on which is stored one or more sets of instructions (e.g., software 1124) embodying any one or more of the methods or functions described herein, including those methods illustrated above. The instructions 1124 may also reside, completely or at least partially, within the main memory 1104, the static memory 1106, and/or within the processor 1102 during execution thereof by the computer system 1100. The main memory 1104 and the processor 1102 also may constitute tangible computer-readable storage media.

Dedicated hardware implementations including, but not limited to, application specific integrated circuits, programmable logic arrays and other hardware devices that can likewise be constructed to implement the methods described herein. Application specific integrated circuits and programmable logic array can use downloadable instructions for executing state machines and/or circuit configurations to implement embodiments of the subject disclosure. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the operations or methods described herein are intended for operation as software programs or instructions running on or executed by a computer processor or other computing device, and which may include other forms of instructions manifested as a state machine implemented with logic components in an application specific integrated circuit or field programmable gate array. Furthermore, software implementations (e.g., software programs, instructions, etc.) including, but not limited to, distributed processing or component/object distributed processing, parallel processing, or virtual machine processing can also be constructed to implement the methods described herein. It is further noted that a computing device such as a processor, a controller, a state machine or other suitable device for executing instructions to perform operations or methods may perform such operations directly or indirectly by way of one or more intermediate devices directed by the computing device.

While the tangible computer-readable storage medium 1122 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA, LTE) can be used by computer system 1100.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. The exemplary embodiments can include combinations of features and/or steps from multiple embodiments. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, can be used in the subject disclosure.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

References cited in the subject disclosure.

[1] Branton, D.; Deamer, D. W.; Marziali, A.; Bayley, H.; Benner, S. A.; Butler, T.; Di Ventra, M.; Garaj, S.; Hibbs, A.; Huang, X.; et. al., The Potential and Challenges of Nanopore Sequencing. *Nature Biotechnology* 2008, 26, 1146-1153.

[2] Manrao, E.; Derrington, I.; Laszlo, A.; Langford, K.; Hopper, M.; Gillgren, N.; Pavlenok, M.; Niederweis, M.; Gundlach, J. Reading DNA at single-nucleotide resolution with a mutant MspA nanopore and phi29 DNA polymerase. *Nature Biotechnology* 2012, 30, 349-353.

[3] Cherf, G.; Lieberman, K.; Rashid, H.; Lam, C.; Karplus, K.; Akeson, M. Automated forward and reverse ratcheting of DNA in a nanopore at 5-A precision. *Nature Biotechnology* 2012, 30, 344-348.

[4] D. Wells, M Belkin, J. Corner and A. Aksimentiev. Assessing graphene nanopores for sequencing DNA. *Nano Letters* 12: 4117-4123.

What is claimed is:

1. A method, comprising:
applying a first electrical potential to a membrane having a nanopore to repel a molecular strand from a top surface and a bottom surface of the membrane, wherein the membrane and the molecular strand are placed in an electrolyte solution;
applying a second electrical potential to the electrolyte solution to apply a transport force on the molecular strand to displace a section of the molecular strand into the nanopore;
arresting the section of the molecular strand in the nanopore by adjusting the first electrical potential to cause the molecular strand to adhere to the top surface and the bottom surface of the membrane and by adjusting the second electrical potential to reduce the transport force; and
measuring a signal at the nanopore to identify the section of the molecular strand.

2. The method of claim 1, comprising:
reapplying the first electrical potential to the membrane to repel the molecular strand from a top surface and a bottom surface of the membrane;
reapplying the second electrical potential to the electrolyte solution to apply the transport force on the molecular strand to displace a new section of the molecular strand into the nanopore;
arresting the new section of the molecular strand in the nanopore by adjusting the first electrical potential to cause the molecular strand to adhere to the top surface and the bottom surface of the membrane and by adjusting the second electrical potential to reduce the transport force; and
measuring a second signal at the nanopore to identify the new section of the molecular strand.

3. The method of claim 2, comprising repeating the reapplying of the first electrical potential, the reapplying of the second electrical potential, the arresting, and the measuring until a desired number of sections of the molecular strand have been identified according to a measured signal.

4. The method of claim 1, wherein the signal comprises an ionic current through the nanopore.

5. The method of claim 1, wherein the signal comprises a transverse current through the membrane.

6. The method of claim 1, wherein the membrane comprises a polymer, and wherein the polymer produces an electric charge responsive to the applying of the first electrical potential, and wherein the polymer has hydrophobic properties.

7. The method of claim 1, wherein the membrane comprises graphene.

8. The method of claim 1, wherein the first electrical potential is produced by a first voltage source, and wherein the second electrical potential is produced by a second voltage source.

9. The method of claim 1, wherein the applying of the first electrical potential comprises applying the first electrical potential for a first period, wherein the applying of the second electrical potential comprises applying the second electrical potential for a second period, wherein the first period exceeds the second period, and wherein at least a portion of the second period overlaps with the first period.

10. The method of claim 1, wherein the arresting comprises adjusting the first electrical potential contemporaneously with adjusting the second electrical potential to arrest the section of the molecular strand in the nanopore.

11. The method of claim 1, wherein the molecular strand comprises one of a biomacromolecule.

12. The method of claim 11, wherein the biomacromolecule comprises one of a deoxyribonucleic acid, a ribonucleic acid, or a protein.

13. A method, comprising:
selectively applying a first electrical potential to a top surface of a membrane having a nanopore to repel or attract a molecular strand from the top surface of the membrane, wherein the membrane and the molecular strand are placed in an electrolyte solution;
applying a second electrical potential to a bottom surface of the membrane to repel or attract the molecular strand from the bottom surface of the membrane;
applying a third electrical potential to the electrolyte solution to apply a transport force on the molecular strand to displace a section of the molecular strand into the nanopore;
arresting the section of the molecular strand in the nanopore by adjusting of the first electrical potential, the second electrical potential, the third electrical potential, or combinations thereof; and
measuring a signal at the nanopore to identify the section of the molecular strand.

14. The method of claim 11, wherein the membrane comprises a first and second layers of a polymer with conductive and hydrophobic properties.

15. The method of claim 14, wherein an insulator is disposed between the first and second layers.

16. The method of claim 15, wherein the insulator comprises a dielectric material, and wherein the first and second layers comprise a graphene material.

17. The method of claim 15, wherein the signal comprises one of an ionic current through the nanopore, a transverse current through the insulator, or a combination thereof.

18. An apparatus, comprising:
- a membrane comprising a through-hole;
- a first voltage source that facilitates application of a first potential to a surface of the membrane to repel a molecular strand from a top surface of the membrane, a bottom surface of the membrane or both, wherein the membrane and the molecular strand are disposed in a solution having conductive properties;
- a second voltage source that facilitates application of a second potential to the solution resulting in a transport force on the molecular strand to displace a section of the molecular strand into the through-hole;
- a controller coupled to the first voltage source and the second voltage source to facilitate adjusting the first potential and the second potential, to arrest the section of the molecular strand in the through-hole; and
- a sensor that facilitates measuring a signal at the through-hole to identify the section of the molecular strand.

19. The apparatus of claim 18, wherein the through-hole is a nanopore.

20. The apparatus of claim 19, wherein the signal comprises one of an ionic current through the nanopore, a transverse current through an insulator, or a combination thereof.

* * * * *